United States Patent [19]

Sethofer

[11] 4,323,473
[45] Apr. 6, 1982

[54] CYCLOHEXYL CYCLOHEXYL DIOXANE LIQUID CRYSTALLINE COMPOUNDS AND ADMIXTURE CONTAINING SAME

[75] Inventor: Nicholas L. Sethofer, San Jose, Calif.

[73] Assignee: Timex Corporation, Waterbury, Conn.

[21] Appl. No.: 226,298

[22] Filed: Jan. 19, 1981

Related U.S. Application Data

[63] Continuation-in-part of Ser. No. 219,672, Dec. 24, 1980, which is a continuation-in-part of Ser. No. 135,381, Mar. 28, 1980, Pat. No. 4,298,528.

[51] Int. Cl.$^3$ .......................... G02F 1/13; C09K 3/34; C07D 319/04
[52] U.S. Cl. .............. 252/299.61; 252/299.1; 260/340.7; 350/349; 350/350 R
[58] Field of Search ............. 260/340.7; 252/299.1, 252/299.61; 350/350 R, 350 S, 349

[56] References Cited

U.S. PATENT DOCUMENTS

| | | | |
|---|---|---|---|
| 4,130,502 | 12/1978 | Eidenschink et al. | 252/299.63 |
| 4,154,697 | 5/1979 | Eidenschink et al. | 252/299.63 |
| 4,181,625 | 1/1980 | Eidenschink et al. | 252/299.63 |
| 4,200,580 | 4/1980 | Hsu | 252/299.61 |
| 4,298,528 | 11/1981 | Sethofer | 252/299.61 |

FOREIGN PATENT DOCUMENTS

| | | | |
|---|---|---|---|
| 139852 | 1/1980 | German Democratic Rep. | 252/299.61 |
| 139867 | 1/1980 | German Democratic Rep. | 252/299.61 |
| 2044767 | 10/1980 | United Kingdom | 252/299.61 |
| 2063288 | 6/1981 | United Kingdom | 252/299.61 |

OTHER PUBLICATIONS

Jorkin, H., Mol. Cryst. Liq. Cryst. (Letters), vol. 56, pp. 279-281 (1980).

*Primary Examiner*—Teddy S. Gron
*Attorney, Agent, or Firm*—William C. Crutcher; Edward J. Timmer

[57] ABSTRACT

Novel liquid crystalline compounds having low viscosity, high (N-I) transition temperatures, positive dielectric anisotropy and low optical birefringence are provided and are represented by the formula:

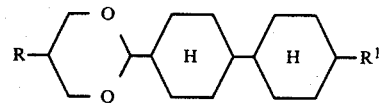

where R and $R^1$ can be the same or different straight chain alkyl or alkoxy group.

Also disclosed are liquid crystalline admixtures having a broad nematic temperature range by virtue of the inclusion therein of the above-described compound. Typical admixtures of the invention include at least one compound of the above formula and at least one compound of the general formula

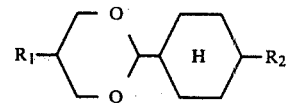

or of the general formula

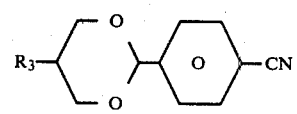

where $R_1$, $R_2$ and $R_3$ can be the same or different alkyl or alkoxy group. These admixtures exhibit low optical birefringence and are useful as the host material in a guest-host electrooptical display.

5 Claims, No Drawings

CYCLOHEXYL CYCLOHEXYL DIOXANE LIQUID CRYSTALLINE COMPOUNDS AND ADMIXTURE CONTAINING SAME

This application is a continuation-in-part of U.S. application Ser. No. 219,672 filed Dec. 24, 1980 which is a continuation-in-part of U.S. application Ser. No. 135,381 filed Mar. 28, 1980, now U.S. Pat. No. 4,298,528.

FIELD OF THE INVENTION

The present invention relates to electrooptical displays especially of the guest-host type and to liquid crystalline admixtures useful in such displays.

DESCRIPTION OF THE PRIOR ART

The family of electrooptical display devices known generally as guest-host devices are thought to have high potential utility for information display purposes such as digital watches or clocks, calculators and other instruments. The typical guest-host device includes a pair of flat, parallel transparent substrates carrying transparent electrode segments on their facing surfaces and a mixture of nematic liquid crystal host compound and guest dichroic dye compound sealed between the substrates and electrodes. In this arrangement, the guest dye molecules tend to assume the orientation of the host liquid crystal molecules relative to the spaced substrates. The construction and operation of such guest-host electrooptical display devices are well known as shown in the Helmeier U.S. Pat. No. 3,551,026 issued Dec. 29, 1970.

In one type of guest-host display, the host liquid crystal molecules and therefore the guest dye molecules are aligned with their long axis parallel (homogenous) to the the spaced substrates in the unactivated (off) state. However, when an electric field is generated across the electrode segment, the liquid crystal molecules align perpendicularly (homeotropically) to the substrates as do the guest dye molecules. Since the dichroic dye molecules absorb only light whose electric vector lies along the long dye axis, the homeotropically aligned dye molecules absorb little light and the liquid crystal-dye mixture between activated electrode segments appears essentially colorless or transparent to the viewer of incident light. Of course, homogenously aligned areas of the mixture appear colored or dark as a result of the perpendicular orientation of the dye molecules to the incident light. A display having light or colorless digits or symbols on a dark or colored background is thereby provided.

However, guest-host display devices of this type suffer from a serious drawback in that, at best, the homogenously aligned dye molecules will absorb only 50% of the light incident upon the device, thereby resulting in poor display contrast. This limitation is due to the fact that only one polarization direction of the incident light has its electric vector aligned along the long axis of the eye molecule while the other polarization direction has its electric vector aligned transverse to the long dye axis. One attempted solution to this drawback has been to use well-known substrate surface alignment techniques such as rubbing or slope evaporation to induce 90° twist (helix) in the long axis of the homogenously aligned liquid crystal molecules from one substrate to the other much as in the well-known twisted nematic liquid crystal electrooptical display devices, for example see the Taylor and White U.S. Pat. No. 3,833,287 issued Sept. 3, 1974 and Coates and Gray U.S. Pat. No. 4,145,114 issued Mar. 20, 1979. The purpose of this helical molecular structure is to ensure that no matter what the orientation of the electric vector of the incident light, there will be a dye molecule at some distance between the spaced sustrates with its long axis parallel to the vector to effect absorption. Thus, absorption of 95% or more of the incident can be effected. Unfortunately, however, as is well known in conventional twisted nematic liquid crystal devices, the host liquid crystal exhibits a positive birefringence and tends to act as an optical waveguide so that the polarization of light transmitted through the device is twisted synchronously with the twist of the long axes of the liquid crystal molecules that the light is passing through. The unfortunate net effect is that the twisted guest-host display made with positive birefringent liquid crystal compounds is optically equivalent to a non-twisted homogeneously aligned guest-host device with the attendant poor contrast.

The possibility of utilizing a host liquid crystal or liquid crystal admixture with minimal birefringent properties in such twisted guest-host display devices in order to increase contrast was initially proposed by Taylor in the *Journal of Applied Physics* 45(11), Nov. 1974 at page 4,721. However, a practical mixture of liquid crystal compounds with low enough birefringence has not up to the present time been known or developed by prior art workers. The cyclohexyl cyclohexane compounds first synthesized by Eidenschink et al., *Angew. Chem.* 133, p. 90 (1978) apparently do not have low enough birefringent properties for twisted guest-host displays and mixtures containing these compounds are sometimes smectic rather than nematic at room temperature.

A copending patent applicant U.S. Ser. No. 136,855 filed Apr. 3, 1980 in the same of Howard Sorkin and of common assignee herewith discloses liquid crystal compounds of the formula:

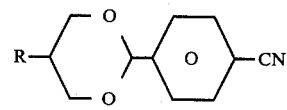

where R is alkyl, alkoxy, aryl, aryloxy, arylister, carboxy or carboxy ester. These compounds have a very low electrical threshold voltage of approximately 0.6 volt, and relatively low optical birefringence of $\Delta n$ equal to 0.1.

The Hsu U.S. Pat. No. 4,200,580 issued Apr. 29, 1980 and of common assignee herewith discloses compounds of the formula:

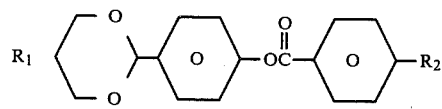

where $R_1$ is a straight chain alkyl of 1 to 10 carbon atmos and $R_2$ is alkyl, alkoxy, acyloxy, alkyl cabonato having 1 to 10 carbons, CN or $NO_2$.

Japanese patent application No. 55-85583 published June 27, 1980 and British application 2,041,354A published Sept. 10, 1980 dislose dioxane compounds having the general formula

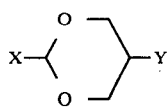

and liquid crystalline admixtures containing such compounds. These applications are foreign counter parts of East German Pat. Nos. 139,852 and 139,867.

What is still needed, however, are liquid crystalline admixtures having broader nematic temperature ranges and having low optical birefringence along with the other required proeprties to provide a guest-host display with improved contrast.

SUMMARY OF THE INVENTION

According to the present invention, there is provided a new group of compounds which exhibit the aforementioned required combination of properties.

The compounds of the invention are represented by the formula:

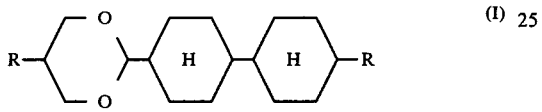

where R and $R^1$ can be the same or different alkyl or alkoxy group.

The present invention also relates to the discovery that compounds of formula I are capable of extending the nematic temperature range of liquid crystalline admixtures.

Preferred admixtures according to the invention include at least one compound of the formula:

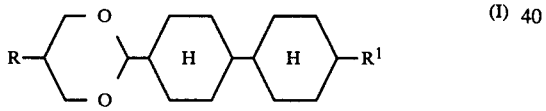

where R and $R^1$ are as described hereinabove, preferably in an amount of at least 20 weight percent, and at least one compound of the formula:

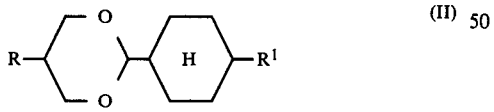

where R and $R^1$ are as described hereinabove or at least one compound of the formula:

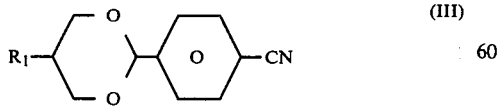

where $R_1$ can be alkyl or alkoxy.

DESCRIPTION OF PREFERRED EMBODIMENTS

The Compound I may be prepared as follows:

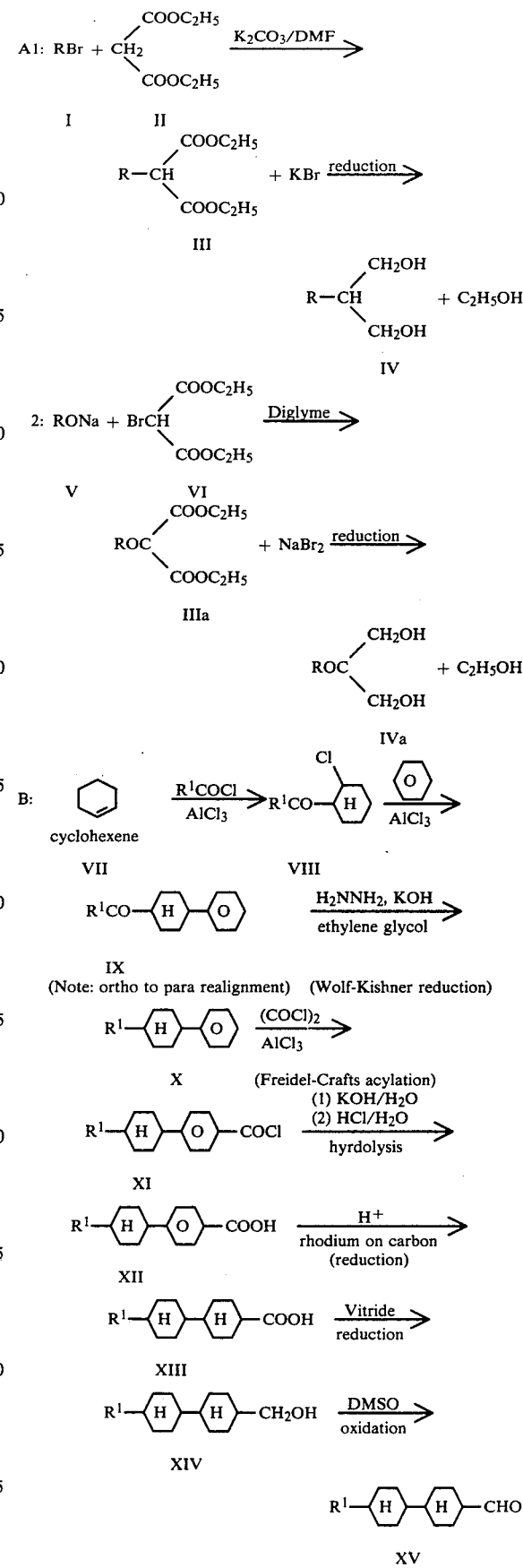

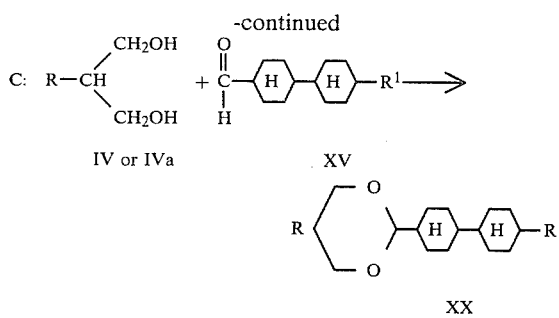

where R, R¹ are as described hereinabove.

The alkylation of malonic acid esters was carried out with potassium carbonate in dimethyl formamide for convenience with the reaction mixture being stirred for one week at room temperature to yield 90% and above of compound III.

The reduction of the R-substituted malonic acid esters was carried out by subsequent reactions with borane methyl suflide complex followed by Vitride reducing agent (e.g., sodium-bis-(2-methoxy-ethoxy) aluminum hydride) or with lithium aluminum hydride in diethyl ester.

The cyclohexene reactant (Compound VII) was either commercially available or prepared according to well-known methods.

Compounds VIII and IX were prepared in one vessel as follows. Cyclohexene, alkyl chloride with aluminum trichloride in an inert solvent such as hexane were reacted at low temperatures, e.g., starting $-60°$ C. gradually increasing to $-40°$ C., and yielded 1-alkyl ketone, 2-chloro-cyclohexane (Compound VII) in the form of a thick oily substance (e.g., see W. S. Johnson et al., J. Am. Chem. Soc., Vol. 67, No. 7, p. 1045 (1945) and C. D. Nenitzescu and I. G. Gavat, Ann. 519,290 (1935). Hexane was then decanted and an excess of benzene with an additional amount of aluminum trichloride was added. The Friedel-Crafts type reaction proceeded at $+45°$ C. to yield compound IX and ortho to para rearrangement takes place according to the literature and my experience.

Compound IX was reduced by the Wolf-Kishner reduction to Compoud X. Then Friedel-Crafts acylation yielded Compound XI. Hydrolysis of the acid chloride (Compound XI) to carboxylic acid (Compound XII) was then effected. These synthesis reactions are well known in the art.

Compound XIII, 4-alkyl or alkoxy bi(cyclohexyl) carboxylic acid, was prepared by hydrogenation using either sodium metal in isoamyl alcohol (trans isomer separated from cis by crystallization in pentane) or, preferably, by catalytic hydrogenation over rhodium on carbon. The resulting predominantly cis isomer was transformed to trans with sodium methoxide in pyrrolidine, although other methods may be employed.

Reduction of the carboxyl groups of compound XIII to methanol to yield compound XIV was carried out with Vitride reducing agent with yields over 95%. Oxidation of compound XIV to alkyl or alkoxy bi(cyclohexyl) carboxaldehyde was then achieved with dimethyl sulfoxide and N,N¹-dicyclohexylcarbodiimide and pyridiniumtrifluoro acetate as the catlyst. A mild, room temperature reaction had yields of 70% and above of compound XI.

The dioxane compounds of the present invention are obtained as both trans and cis isomers, typically in 3:1 ratio. The isomers can be readily separated by crystallization from hexanes, pentanes or other well-known solvents. The trans configuration is the one which presumably accounts for the nematic characteristics of the subject compounds.

The following examples are offered for purposes of illustration, rather than limitation, and provide a more detailed description of the preparation dioxane compounds. EXAMPLE I 5-Ethyl-2-(4-(4-Pentylcyclohexyl) cyclohexyl)-1,3-Dioxane A. Formation of 2-ethyl,1,3-propane diol In this particular instance, alkylation of diethyl malonate (II) to 2-ethyl-1,3 diethyl malonate (III) was not necessary as it is available from Aldrich Chemical company under catalog #D, 9,520-4.

Reduction of compound III to 2-ethyl-1,3-propane diol (IV) has been performed with lithium aluminum hydride in diethyl ether by the method described in Fieser & Fieser: "Reagents for Organic Synthesis," Vol. 1, p. 584.

B. Trans-4-(4-Pentylcyclochexyl)-cyclohexane carboxylic acid

Introduce approximately 500 ml of hexane into 3-neck flask fitted with air-driven stirrer and thermometer, all fitted into appropriate cooling bath. Cool the solvent to $-60°$ C. and then add 82.2 g (1 mole) of cyclohexene, 160 g (1.2 mole) of AlCl₃ anhydrous and, 145 g (1.2 mole) of valeryl chloride. Stir for 3½ hours while raising temperature slowly to $-40°$ C. Then discontinue stirring and decant solvent from thick oily substance. Wash at least once with cold hexane and then react 1-pentanone-2-chloro cyclohexane (VIII) with excess of benzene (approximately 500 ml) and additional AlCl₃ (approximately 60 g), i.e. less than 0.5 mole. Stir for 3½ hours at a temperature of $+45°$ C. Then cool down to room temperature, pour over water with ice, separate layers and evaporate excess of benzene. Yield of compound IX, 4-heptanoylcyclohexyl benzene varies from 75 to 80% with a trans/cis ratio 2.5 to 1.5. separation of isomers was not done at this stage.

NOTE: Literature (1) and (2) reported that compound IX assumed para position from ortho, exhibited in compound VIII. My experience with above reaction is in full agreement, i.e., no ortho IX isomer was detected.

Following Wollf-Kishner reduction X, the Friedel-Crafts acylation XI and hydrolysis XII are routine types of synthesis and are well know to those skilled in the art.

Catalytic hydrogenation of 4-(4-pentylcyclohexyl) benzoic acid was done over rhodium on carbon at low temperatures and hydrogen pressures to yield predominantly cis isomer of 4-(4-pentylcyclohexyl) cyclohexane carboxylic acid (XIII). Cis isomer was transformed to trans by well know method with sodium methoxide in pyrrolidine, although other methods may be employed. Remaining few percents of cis isomer were removed by crystallization from hexane.

(C) Trans-4(4-pentylcyclohexyl) cyclohexane carboxaldehyde

Introduce about 200 ml of benzene and 27.5 g of compound XIII (0.1 mole) into 3-neck flask fitted with a condenser and air-driven stirrer and bring to reflux. Within 30 minutes, add dropwise a solution of 90 ml of Vitride (i.e., sodium-bis (methoxy-ethoxy) aluminum hydride) and about 150 ml of benzene and continue to reflux for additional 3–4 hours. Mixture is then cooled to room temperature and carefully poured, with vigorous stirring, over a 20% HCl aqueous solution plus ice. After additional 20–30 minutes stirring the resulting layers are separated, solvent evaporated.

Purification of the trans-4(pentylcyclohexyl) cyclohexane methanol XIV) was not necessary, as gas chromatography showed 99.9% purity while yield was in excess of 95%.

The next step involved mixing the following in a suitable flask with a magnetic stirring bar:
(1) 23.5 g (0.09 mole) of compound XIV
(2) about 150 ml benzene
(3) about 150 ml (excess) dimethyl sulfoxide (DMSO)
(4) 7.5 ml (0.09 mole) pyridine
(5) 3.6 ml (0.045 mole) trifluoroacetic acid
(6) 56 g (0.27 mole ) $N_1N^1$-dicyclohexyl carbodiimide (DCC)

The flash was sealed with a drying tube and the mixture stirred at 40°–45° C. for 16 hours. Oxalic acid is then added in small portions (foaming occurs) until excess of DCC is destroyed and then mixture is filtered and the solid portion is washed several times with benzene.

The organic filtrate is washed with a solution of sodium bicarbonate and several times with water to remove most of the excess of DMSO. If necessary, crude aldehyde is purified via complex with sodium bisulfite.

The trans 4-(4-heptylcyclohexyl) cyclohexane carboxaldehyde obtained had 94% purity by GC and yield was 78%.

(D)
5-ethyl-2(4-(pentylcyclohexyl)cyclohexyl)-1,3-dioxane

To a 3-liter, 3-neck round bottom flask fitted with a Dean-Stark trap condenser and stirrer, the following are introduced:
(1) 16 g (0.15 mole) 3-ethyl-1,3-propane diol
(2) 26 g (0.1 mole) trans-4(4-pentylcyclohexyl) cyclohexane carboxaldehyde
(3) 400 ml benzene
(4) trace p-toluene sulfonic acid.

The mixture is brought to reflux and the water removed azeotropically. Refluxing is continued for 6–8 hours, then the benzene is removed by evaporation and residue checked by GC. The raw compounds are found to contain two main portions with identical infrared spectra (combined 90% yield). The ratio of trans/cis isomers was found to be in excess of 3:1.

Separation of isomers was carried out by crystalization from ethanol, repeated 3–4 times with one decolorizing carbon treatment. Purification yielded only one peak on GC.

Transition temperatures for trans-5-ethyl-2-(4-(4-pentylcyclohexyl) cyclohexyl)-1,3-dioxane as measured on a Perkin-Elmer DSC-2instrument were as follows:
(C-S)=41.6° C. (crystal to smectic)
(S-N)=177.7° C. (smectic to nematic)
(N-I)=181.3° C. (nematic to isotropic liquid)
NOTE: Even though measured smectic phase is considerably broad and nematic range rather narrow, it was interesting to find out that none of evaluated mixtures described hereinafter exhibited smectic phase within the calculated range.

EXAMPLE II 5-propyl-2-(4-(4-pentylcyclohexyl) cyclohexyl)-1,3-dioxane
(C-S)=77.8° C.
(S-N)=196.4° C.
(N-I)=198.6° C.

An example of the efficacy of compounds of the invention (compound I) in broadening the nematic temperature range of admixtures including two ring cyclohexyl dioxane compounds is as follows. A binary eutectic mixture comprising 0.745 mole fraction of 5-ethyl-2-(4-pentylcyclohexyl)-1,3-dioxane (compound A) and 0.255 mole fraction of 5-propyl-2-(4-heptylcyclohexyl)-1,3 dioxane (compound B) exhibits a nematic temperature range of 12.5° C. to 26.5° C. Addition of a three ring compound of the formula

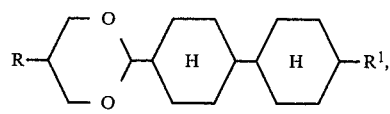

namely, 5-ethyl-2-(4-pentylcyclohexyl) cyclohexyl)-1,3 dioxane (compound C) to provide a eutectic mixture comprising 0.610 mole fraction of compound A, 0.189 lmole fraction of compound B and 0.201 mole fraction of compound C resulted in a measured nematic temperature range of 8.6° C. to 59.7° C. while the mixture retained low viscosity and low optical birefringence, e.g., Δn=0.04.

Another example of mixture of compounds of the invention with cyclohexyl dioxanes:

| Structure | Weight % |
|---|---|
| $C_2H_5$—dioxane—cyclohexyl—$C_5H_{11}$ | 41.6 weight % |
| $C_3H_7$—dioxane—cyclohexyl—$C_5H_{11}$ | 25.0 weight % |
| $C_3H_7$—dioxane—cyclohexyl—$C_7H_{15}$ | 12.7 weight % |
| $C_2H_5$—dioxane—cyclohexyl—cyclohexyl—$C_5H_{11}$ | 20.7 weight % |

(C—N) = −4.8° C. (crystal to nematic)
(N — I) = 62.3° C.

Electrooptical properties (11 to 12 micron spacing of cell, high/low SiO evaporation, crossed polarizers):
$V_{10\%}$=2.75 V (10% saturation voltage)
$V_{90\%}$=4.45 V (90% saturation voltage)
Δn=0.04

Examples of a cyanophenyl dioxane eutectic mixture and the same with the addition of compounds of invention are as follows:

(1)

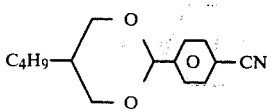 30.3 weight %

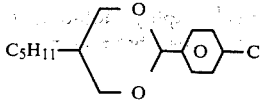 21.1 weight %

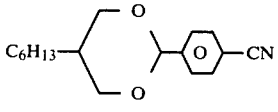 28.2 weight %

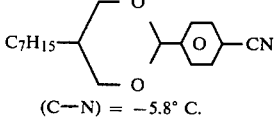 20.4 weight %

(C—N) = −5.8° C.
(N − 1) = 40.1° C.

(2)

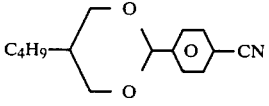 24.6 weight %

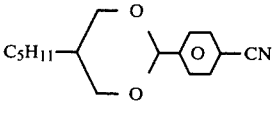 16.7 weight %

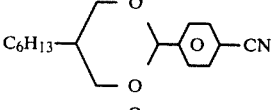 22.5 weight %

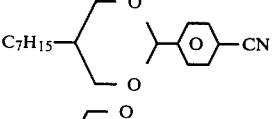 15.9 weight %

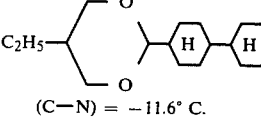 20.3 weight %

(C—N) = −11.6° C.
(N − 1) = 63.2° C.

Above mixtures 1 and 2 were calculated by Schroder-van Laar equation programmed to HP9825A computer.

Compounds II (cyclohexyl dioxanes) of the admixtures can be prepared as taught in copending U.S. application Ser. No. 135,381 filed Mar. 28, 1980, the disclosure of which is hereby incorporated by reference.

Compounds III (cyanophenyl dioxanes) can be prepared as taught in the copending U.S. application Ser. No. 136,855 filed Apr. 3, 1980 and the East German Pat. Nos. 139,852 and 139,867, the disclosures of which are incorporated herein by reference.

The compounds used in the admixtures above can be conveniently prepared as follows:

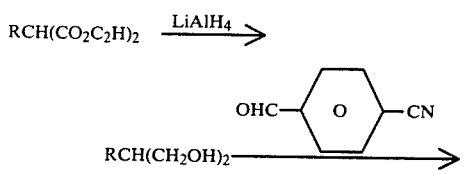

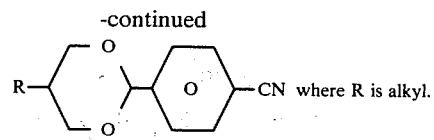 where R is alkyl.

While the invention has been explained by a detailed description of certain specific embodiments it is understood that various modifications can be made in them within the scope of the appended claims which are intended to include equivalents of such embodiments.

I claim:

1. A nematic liquid crystalline admixture including as an effective ingredient to broaden the nematic temperature range a compound of the formula:

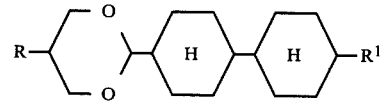

where R and R$^1$ independently can be the same or different straight chain alkyl or alkoxy group.

2. The admixture of claim 1 wherein the said compound is present in an amount of at least 20 weight percent.

3. A nematic liquid crystalline admixture comprising at least one compound of the formula:

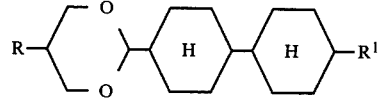

where R and R$^1$ can be the same or different straight chain alkyl or alkoxy groups and further comprising at least one compound of the formula (a):

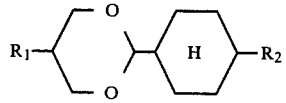

where R$_1$ and R$_2$ can be the same or different straight chain alkyl or alkoxy group or the formula (b):

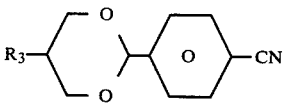

where R$_3$ can be an alkyl or alkoxy group.

4. A nematic liquid crystalline host admixture for a guest-host electrooptical display having an optical birefringence of 0.05 or below comprising at least one compound of the formula:

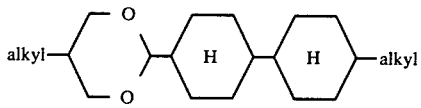

and further comprising at least one compound of the formula (a):

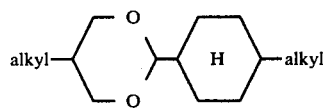
or of the formula (b):
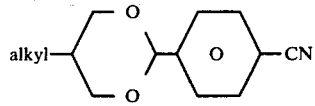
5. A guest-host electrooptical display including the admixture of claim 1, 2, 3 or 4 as the host material.
* * * * *